United States Patent [19]

Stine

[11] 4,307,288

[45] Dec. 22, 1981

[54] STERILIZER

[75] Inventor: Orrin B. Stine, Chicago, Ill.

[73] Assignee: Wesley-Jessen Inc., Chicago, Ill.

[21] Appl. No.: 762,176

[22] Filed: Jan. 24, 1977

[51] Int. Cl.³ .......................... A61L 2/04; A61L 2/06; A61L 2/24; H05B 3/06

[52] U.S. Cl. ................................. 219/521; 219/399; 422/109; 422/302

[58] Field of Search ................... 21/85, 86, 89, 90, 93; 219/521, 385, 399; 422/109, 300, 302

[56] References Cited

U.S. PATENT DOCUMENTS

| | | |
|---|---|---|
| 1,780,462 | 11/1930 | Carmean et al. |
| 1,946,573 | 2/1934 | De Vries |
| 2,091,035 | 8/1937 | Foster |
| 2,552,641 | 5/1951 | Morrison ............................. 219/521 |
| 2,656,441 | 10/1953 | Slatkin |
| 3,801,278 | 4/1974 | Wagner et al. ........................ 21/86 |
| 3,961,893 | 6/1976 | Russell et al. ........................ 21/95 |
| 3,977,517 | 8/1976 | Kadlecik et al. |
| 3,983,362 | 9/1976 | Hoogesteger et al. ................ 21/85 |
| 4,044,226 | 8/1977 | Kadlecik et al. ..................... 422/1 |

*Primary Examiner*—Bradley R. Garris

*Attorney, Agent, or Firm*—Warrick E. Lee, Jr.; Vincent H. Gifford; Bruce M. Eisen

[57] ABSTRACT

A sterilizer for use in sterilizing articles removably received therein, includes first thermal insulating means with a receiving cavity formed therein; cover means including a second thermal insulating means, the cover means being movable with respect to the first means for selectively covering said cavity; heating means received within the cavity and defining recess means for removably receiving therein an article to be sterilized, the heating means having a preselected volume for relatively slowly dissipating heat; and power control means for selectively applying electrical power to the heating means for heating the heating means, and for automatically cutting off the power to the heating means in response to a first predetermined temperature being reached by the heating means, the combination of the heating means and the first and second insulation means resulting in a relatively slow rate of heat loss from the heating means for enabling the temperature of the heating means not to fall below a second predetermined temperature, until a measured period of time elapsed after the electric power has automatically been cut off to the heating means.

5 Claims, 1 Drawing Figure

STERILIZER

FIELD OF THE INVENTION

In general, the present invention relates to sterilizer devices. Specifically, it is directed to a simple, inexpensive and reliable electrically heated sterilizer for purposes of sterilizing contact lenses and the like.

BRIEF DESCRIPTION OF THE PRIOR ART

Sterilizing is a rather standard industrial and commercial practice employed for purposes of aseptizing various kinds of articles and instruments. Particularly, referring to the field of ophthalmology, it is conventional to sterilize contact lenses, such as of the hydrophilic kind. Heretofore, there have been various types of apparatuses proposed for accomplishing the foregoing.

Earlier attempts to achieve sterilization include sealing the lenses in appropriate vials or containers which contain a suitable saline solution. The vials were, in turn, placed in a water bath. Such water baths, however, suffer from the disadvantage that the sterilizing temperatures only reach approximately 100° C. Consequently, of course, the vials and the contact lenses may not be properly treated. Another known general type of apparatus employed to achieve higher temperatures is described in U.S. Pat. No. 1,946,573. As taught in the above referenced patent, such apparatus utilizes electricity to convert a measured quantity of liquid into steam or vapor. The resulting steam or vapor, of course, sterilizes the instruments and the like at a temperature above 100° C. As recognized, a shortcoming associated with the use of this category of sterilizer is the somewhat cumbersome and tedious operation associated with continually refilling the apparatus with water. Often, many of these known conventional sterilizers include suitable timer mechanisms which normally comprise a timer motor and timer switch. Such mechanisms essentially serve to control the supply of electrical power to heating elements for prescribed cycles of operation. Undesirably, the standard timer mechanism, however, invariably results in a sterilizer which is relatively more costly to manufacture. It should be understood that in the highly competitive sterilizer market, the profit margin is considerably small. As a consequence thereof, unnecessarily expensive components have a tendency to somewhat detract from the overall commercial appeal for such a sterilizer.

Still another heretofore known type of sterilizing apparatus which is especially suitable for sterilizing sealed vials that may contain contact lenses is basically set forth in U.S. Pat. No. 3,801,278. As essentially described, such apparatus includes two separated compartments, each having an electrically heated block made of heat conducting material. A single timer mechanism is associated with both heating blocks for purposes of controlling electric power thereto. By this particular arrangement, temperatures of up to 124° C. may be obtained. It is, of course, appreciated that such apparatus overcomes certain of the disadvantages of various prior art sterilizing apparatuses which rely on heated water baths, or steam and vapor. While the foregoing apparatus is somewhat of an improvement over known sterilizers, particularly those for contact lenses and the like, it is not, however, altogether entirely satisfactory. The foremost drawback of such a sterilizer, apart from its relatively complicated construction, is the fact that it is dependent upon a timer motor and switch in order to ensure completion of an adquate sterilization cycle for the contact lenses. By virtue of the inclusion of such a timer mechanism, the resultant costs for construction of the sterilizer are, of course, increased. As aforementioned, cost factors are especially significant in the highly competitive field of sterilizers. Accordingly, this particular sterilizing apparatus does not effectively complete a predetermined sterilization cycle without the necessity of a timer mechanism.

In view of the general comments directed towards the various prior art approaches for sterilizing different kinds or articles and, in particular, contact lenses, it will be recognized that none have been able to achieve, in a simple and reliable fashion, successful heating and sterilizing of the lenses for a predetermined time period so as to complete the sterilizing cycle without the necessity of a relatively costly timer mechanism.

SUMMARY OF THE INVENTION

It is an object of the instant invention to provide a novel and improved sterilizer apparatus which overcomes the previously discussed drawbacks associated with heretofore known apparatuses by providing a sterilizer which is simple in construction and operation, inexpensive in manufacture, reliable in use and does not necessitate use of relatively expensive components, such as a timer mechanism for ensuring completion of a sterilizing cycle.

In accordance with the present invention, there is provided a sterilizer particularly adapted for use in sterilizing articles removably received therein. Such sterilizer includes first thermal insulating means with a receiving cavity formed therein; cover means including a second thermal insulating means and being movable with respect to the first means for selectively covering the cavity; heating means received within the cavity and defining recess means for removably receiving therein an article to be sterilized, the heating means has a preselected volume for relatively slowly dissipating heat; and power control means for selectively applying electrical power to the heating means for heating the heating means, and for automatically cutting off the electrical power to the heating means in response to a first predetermined temperature being reached by the heating means. The combination of the heating means and the first and second thermal insulating means results in a relatively slow rate of heat loss from the heating means for enabling the temperature of the heating means not to fall below a second predetermined temperature, until a measured period of time has elapsed after the electrical power has been automatically cut off to the heating means.

BRIEF DESCRIPTION OF THE DRAWING

The above, as well as other objects, features, and advantages of the novel and improved sterilizing apparatus of this invention will become readily apparent upon a detailed reading of a description thereof when viewed in conjunction with the accompanying drawings wherein like reference numerals indicate like structure throughout the several views.

DETAILED DESCRIPTION

Figure 1:
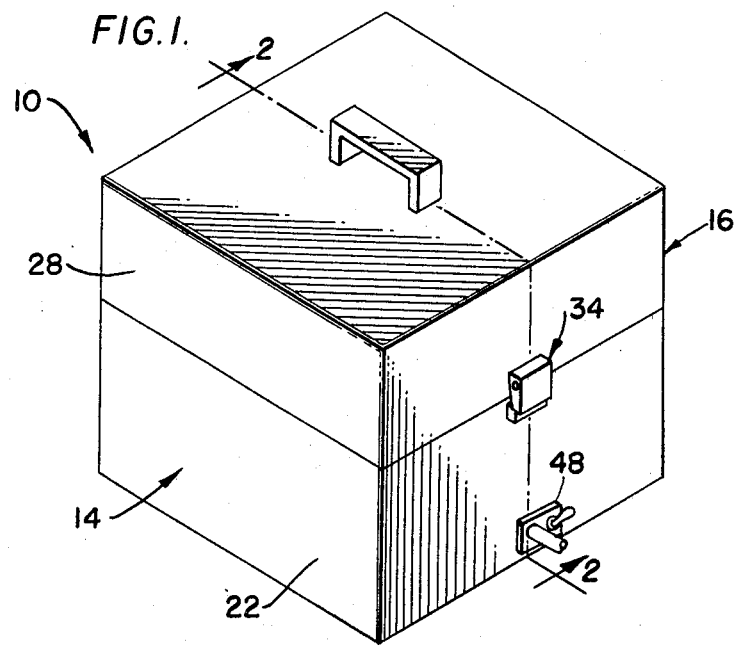
FIG. 1 is a perspective view of the sterilizing apparatus embodying the principles of the present invention.
Figure 2:
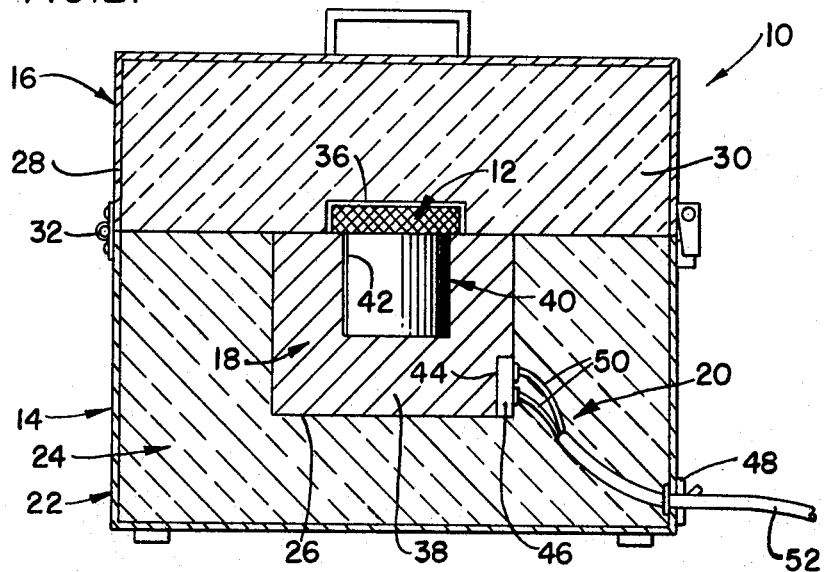
FIG. 2 is a cross-sectional view taken substantially along the section line 2—2 appearing in FIG. 1 illustrating in greater detail certain aspects of the present invention.
Figure 3:
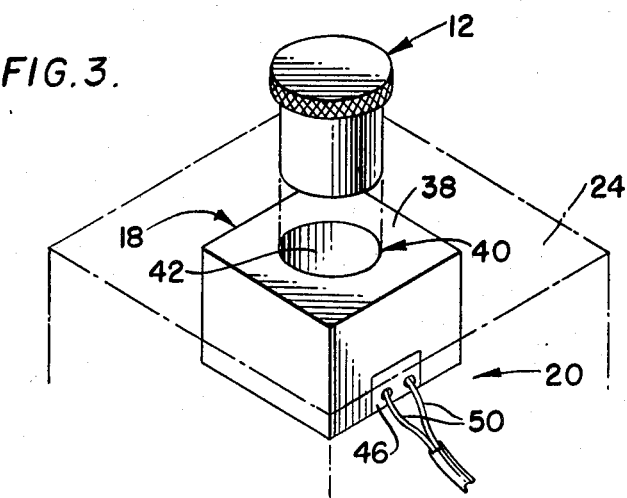
FIG. 3 is a fragmentary perspective view illustrating in somewhat greater detail the heating block of this invention and a vial which is removably received therein.

Referring to FIGS. 1 to 3, there is illustrated a novel and improved sterilizing apparatus of the present invention being designated in general by reference numeral 10. The present invention contemplates that the sterilizer 10 be particularly adapted for use in sterilizing vials 12 containing contact lenses (not shown). Of course, it should be understood that other articles, containers, instruments, and the like may also be sterilized by sterilizer 10 without departing from the spirit and scope of this invention.

Essentially, hereinafter described, the sterilizing apparatus 10 includes base means 14, cover means 16, heating means 18 and power control means 20.

In regard to base means 14, it is defined by a casing member 22 made of a suitable material. In the embodiment being described, casing member 22 has assumed a generally rectangular configuration. Other shapes and sizes for the casing member 22 may, of course, be suitably employed. The casing member 22 itself securely receives therein thermal insulating block member 24. While in the present embodiment the casing member 22 and block members 24 are disclosed as being made of separate material, it will, however, be pointed out that this invention envisions that the casing member can be similarly fabricated from a suitable insulating material. Such thermal insulating block member 24 is fabricated from any conventional type of available thermal insulating material, such as suitable fiber. Instead of a block member air can also be used. Essentially, block member 24 serves to significantly inhibit the dissipation of heat in a manner to be afterwards explained. Preferably, the material should be selected so that it has a relatively low thermal conductivity. In this manner, it will be able to slow the conductivity of the heat. Centrally formed within insulating block member 24 is a cavity 26 which is adapted to receive heating means 18. Although a single cavity 26 is disclosed, a plurality of such cavities may be formed. Moreover, the cavities may have any desired configuration. As will be presently explained in greater detail, the thermal properties of thermal insulating block member 24 and its volume with respect to and in combination with the heating means are of significant importance in regulating the rate of temperature decline of the heating means 18.

In connection with cover means 16, it is configured in a similar fashion to the base means 14 so as to substantially cover the latter. Cover means 16 includes an outer casing member 28 and a block 30 of thermal insulating material snugly received within casing member 28. Likewise with respect to casing member 28 and block 30, instead of being constructed separately both can be fabricated such that the casing member is also made from the same insulating type material as the insulating block. The cover means 16 is removably associated with the base means 14. In the present embodiment, a standard type of hinge device 32 operatively interconnects the casing member 22 and casing member 28 so as to enable the casing member 28 to be pivoted between open and closed positions. In addition, both casing members 22 and 28, respectively, may have associated therewith any well-known kind of releasable latching mechanism 34 which serves the purpose of removably attaching the cover means 16 to the base means 14, such as depicted in FIG. 2. The insulating block member 30 is formed with a central relatively shallow recess 36 which is adapted to receive the top portion of vial 12, whenever both the base means 14 and cover means 16 are in their assembled and closed position. It will be understood, of course, that although insulating block 30 is formed with shallow recess 36, such recess need not be formed. On the other hand, of course, the insulating blocks 24 or 30 could also be appropriately constructed so as to completely and suitably receive the vials 12 therein. Thermal insulating block member 30 is fabricated from a suitable thermal insulation material, preferably having a low thermal conductivity value. The significance of this will also be subsequently set forth. Also, as will become evident, the insulating block members 24 and 30 should be fabricated from a material which, in addition to being thermally insulating, is suitably electrically insulating. In addition, the casing members 22 and 28 are envisioned to be electrically insulated for reasons made evident.

With reference to the heating means 18, such is best shown in FIG. 2 taken in conjunction with FIG. 3. As depicted, it is defined by a heating block 38 having a relatively large volume, with respect to the vial 12 and insulating block members 24 and 30, and generally cubical shape. The present invention contemplates, of course, that the heating block need not necessarily be large so long as it, in conjunction with the insulating material, effectively slows down the rate of dissipation of heat within prescribed limits. The heating block 38 is sized and configured so as to be easily and loosely fit within cavity 26. In this manner, expansion thereof resulting from generation of heat is somewhat accommodated for. In the present embodiment, block 38 has a relatively large volume and the significance of this large volume will be presently mentioned. Recess means 40 is defined by an appropriately dimensioned opening 42 formed on the top surface of heating block 38. Opening 42 is adapted to removably receive therein vial 12 during the sterilization cycle. Although a single opening 42 is depicted, it is within the spirit of the invention that a plurality of similar openings may also be included. A cutout 44 may be formed along the bottom of the heating block 38. In this particular embodiment, heating block 38 is comprised of any suitable type of heat conducting material. Accordingly, whenever electric power is supplied to the heating block 38, the latter will be correspondingly heated. In response to heating of block 38 to a sufficient sterilization temperature, the contents of vial 12 can be sterilized.

As previously mentioned, the heating block 38 is constructed to be relatively large. The foregoing is, preferably, done in order to form a heat reservoir which is able to advantageously retain an adequate supply of heat for a prescribed period of time. Since a relatively great quantity of heat is being retained, it will be appreciated, of course, that heat dissipation will correspondingly take longer to occur. The present invention contemplates that the insulating block members 24 and 30, respectively, have their appropriate volumes and values of thermal conductivity selected such that the dissipation of heat from heating reservoir block 38 is substantially impeded. In this particular manner, with a relatively long period of heat dissipation from heating block 38, in conjunction with a significant reduction in heat flow rate provided by the insulating member blocks 24 and 30, a relatively long period of time is required for the heating block to dissipate a substantial amount of heat. Stated somewhat differently, the rate of temperature reduction of heating block 38 is relatively slowed.

In the present invention, it is envisioned that the rate of temperature reduction from heating block 38 occur such that after the temperature value thereof has reached a first predetermined temperature, usually above a sufficient sterilization temperature for contact lenses or the like, it gradually falls to a second or minimum predetermined temperature, usually above the same sterilization temperature, during a preselected period of time. As indicated in the instant embodiment, such minimum temperature value may be selected such that it will at least ensure sterilization of contact lenses in vial 12. The measured period of time may be that which at least successfully ensures completion of the sterilization process for contact lenses. Towards this particular end of achieving such minimum temperatures for the measured period of time, it should be recognized that the selected first or maximum temperature reached by the heating block 38, the volume of the heating block and its thermal properties together with the thermal properties and volume of insulating block members 24 and 30 will be appropriately selected consistent with sound engineering practice to achieve the foregoing objective. Of course, it will be appreciated that a number of materials may be appropriately employed without departing from the spirit and scope of the instant invention. By way of specific example and not limitation, it has been determined that if the heating block 38 has its temperature drop from 270° F. to 240° F. in twenty minutes such would be adequate for successfully sterilizing contact lenses. Accordingly, it becomes quite evident that sterilizer 10 of the instant invention permits conditions under which contact lenses within vials 12 may be sterilized for an appropriate period of time without the necessity of a relatively expensive timer mechanism. Hence, a relatively inexpensive and simple constructed sterilizer can be constructed in accordance with this invention.

Referring now to the electrical power control means 20, such is seen to include a thermal cutout device 46 and power switch 48. Both the thermal cutout 46 and switch 48 are of conventional construction and are designed to control the electric power supplied to heating block 38. Thermal cutout device 46 is attached, in any suitable manner, to the cutout 44 formed in heating block 38, and functions in the normal fashion to stop the flow of current to block 38, in event the heating block reaches a preselected temperature. Of course, thermal cutout 46 may be received within a cutout area of insulating block member 24 as opposed to cutout 44 in heating block 38. The preselected temperature at which thermal cutout 46 functions to stop electrical power may be a first predetermined temperature which is of such a value that it will be sufficient in conjunction with the heat dissipation rate determined by the volumes and materials of a heating block 38 and insulating block members 24 and 30, to ensure that a second or predetermined minimum temperature value will not be reached until a measured period of time has at least elapsed following the cessation of electrical power to the heating block 38. In this embodiment, as indicated, the selected period of time is designed to ensure sterilization of contact lenses in vial 12.

As noted in FIGS. 2 and 3, lead wires 50 are electrically operatively interconnected between thermal cutout 46 and switch 48 in any suitable fashion. The switch 48, in turn, may be connected to a power supply line 52 which supplies electrical power from a suitable source (not shown). The present invention envisons that either a DC or AC source can be utilized. While a switch 48 is shown in the present embodiment, sterilizer 10 may be successfully used without such a switch.

Having thus explained the aforenoted constructional arrangement of the instant embodiment, its operation will be briefly set forth. The vial 12 containing contact lenses is inserted within opening 42. Switch 48 is actuated so as to permit current to flow to heating block 38. Heating block 38 will be heated to a preselected temperature value whereupon the thermal cutout 46 cuts off the supply of electrical power thereto. Since the volume of the heating block 38 may be relatively large and functions as a heat reservoir together with the fact that the volume and thermal insulation characteristics of insulating blocks 24 and 30 are appropriately selected, in the manner indicated above, the dissipation of heat from heating block 38 occurs gradually. During this gradual reduction in temperature, sterilization of the lenses in the vial 12 can occur. As noted, this reduction in temperature will be for a predetermined amount of time above a minimum preselected temperature value so as to ensure completion of a sterilization cycle. After the heating block 38 has been sufficiently cooled, the vials 12 may be removed. It will be appreciated that the sterilizer of this invention can be used for dry sterilization or autoclaving.

While the invention has been described in connection with a preferred embodiment, it is not intended to limit the invention to the particular form set forth, but, on the contrary, it is intended to cover such alternatives, modifications, and equivalents as may be included within the spirit and scope of the invention as defined by the appended claims.

What is claimed is:

1. A sterilizer for use in sterilizing articles removably received therein, including a first volume of thermal insulating means with a receiving cavity formed therein; cover means including a second volume of thermal insulating means, said cover means being movable with respect to said first means for selectively covering said cavity; heating means received within said cavity and defining recess means for removably receiving therein an article to be sterilized, said heating means having a preselected volume relative to said first and second volumes of thermal insulating means for relatively slowly dissipating heat; and power control means for selectively applying electrical power to said heating means for heating said heating means and for automatically cutting off the power to said heating means in response to a first predetermined temperature being reached by said heating means, the combination of the volume of said heating means and the volume and thermal conductivity of said insulating means resulting in a relatively slow rate of heat loss enabling the temperature of said heating means not to fall below a second predetermined temperature, which is lower in value than the first predetermined value, until a measured period of time has elapsed after the electric power has automatically been cut off to said heating means, whereby said second predetermined temperature remains above sterilization temperature for a time sufficient to effect sterilization.

2. A sterilizer for use in sterilizing articles removably received therein, including base means having a first thermal insulating block member having a predetermined volume and with a receiving cavity formed within said first block member; cover means including a second thermal insulating block member having a predetermined volume, said cover means being movable with respect to said base means for selectively covering said cavity; heating means received within said cavity and defining recess means for removably receiving therein an article to be sterilized, said heating means having a preselected volume relative to the volumes of said first and second block members for relatively slowly dissipating heat; and power control means for selectively applying electrical power to the said heating means for heating said heating means and for automatically cutting off the power to said heating means in response to a first predetermined temperature being reached by said heating means, said first and second insulating block members having relatively low thermal and electrical conductivity such that the combination of the ratio of the volume of said heating means to the volume of said insulating block members results in a relatively slow rate of heat loss enabling the temperature of said heating means not to fall below a second predetermined temperature, which is lower in value than the first predetermined temperature value, until a measured period of time has elapsed after the electric power has automatically been cut off to said heating means, whereby said second predetermined temperature remains above sterilization temperature for a time sufficient to effect sterilization.

3. A sterilizer as set forth in claim 2 in which said heating means includes a relatively large metallic block which serves as a heat reservoir.

4. A sterilizer as set forth in claim 3 in which said control means includes at least a thermal cutout device operatively connected to said metallic block for stopping flow of electrical power thereto in response to said first predetermined temperature value of the block being reached.

5. A sterilizer for use in sterilizing articles removably received therein, including base means having a first thermal insulating block member having a predetermined volume and with a receiving cavity formed within said first block member; cover means including a second thermal insulating block member of predetermined volume and being movable with respect to said base means for selectively covering said cavity; heating means received within said cavity and defining recess means for removably receiving therein an article to be sterilized, said heating means includes a relatively large block having a preselected volume relative to the volumes of said first and second block members and which serves as a heat reservoir for relatively slowly dissipating heat; and power control means for selectively applying electrical power to the said heating means for heating said heating means, and including at least a thermal cutout device operatively connected to said metallic block for automatically stopping flow of electrical power thereto in response to a first predetermined temperature being reached by said metallic block, said first and second insulating block members having a relatively large volume and relatively low thermal and electrical conductivity such that the combination ratio of the volume of said heating means to the volume of said insulating block members results in a relatively slow rate of heat loss enabling the temperature of said heating means not to fall below a second predetermined temperature, which is lower in value than the first predetermined temperature, until a measured period of time has elapsed after the electric power has automatically been cut off to said heating means, whereby said second predetermined temperature remains above sterilization temperature for a time sufficient to effect sterilization.

* * * * *